United States Patent [19]
Ikegaki et al.

[11] Patent Number: 5,747,507
[45] Date of Patent: May 5, 1998

[54] CARDIO-PROTECTIVE AGENT

[75] Inventors: Ichiro Ikegaki, Miyazaki-ken; Toshio Asano, Shizuoka-ken, both of Japan

[73] Assignee: Asahi Kasei Kogyo Kabushiki Kaisha, Osaka, Japan

[21] Appl. No.: 379,561

[22] PCT Filed: Aug. 10, 1993

[86] PCT No.: PCT/JP93/01128

§ 371 Date: Feb. 9, 1995

§ 102(e) Date: Feb. 9, 1995

[87] PCT Pub. No.: WO94/03171

PCT Pub. Date: Feb. 17, 1994

[30] Foreign Application Priority Data

Aug. 10, 1992 [JP] Japan .................. 4-212680

[51] Int. Cl.$^6$ .................. A61K 31/47
[52] U.S. Cl. .................. 514/312
[58] Field of Search .................. 514/312

[56] References Cited

U.S. PATENT DOCUMENTS

| | | |
|---|---|---|
| 4,456,757 | 6/1984 | Hidaka et al. . |
| 4,525,589 | 6/1985 | Hidaka et al. . |
| 4,560,755 | 12/1985 | Hidaka et al. . |
| 4,634,770 | 1/1987 | Hidaka et al. . |
| 4,678,783 | 7/1987 | Hidaka et al. . |
| 4,943,581 | 7/1990 | Hidaka et al. . |

FOREIGN PATENT DOCUMENTS

| | | |
|---|---|---|
| 457 295 A2 | 11/1991 | European Pat. Off. . |
| 60-81168 | 5/1985 | Japan . |
| 2-256617 | 10/1990 | Japan . |
| 2-273610 | 11/1990 | Japan . |
| 4-264030 | 9/1992 | Japan . |

OTHER PUBLICATIONS

H CA Plus Abstract 117:124238 (1992).

T. Asano et al., Vasodilatory Action of HA1004 [N–(2–Guanidinoethyl)–5–Isoquinolinesulfonamide], A Novel Calcium Antagonist With No Effect On Cardiac Function, J. Pharmacol Exp. Ther., vol. 231, 1984, pp. 141–145.

T. Asano et al., Intracellular Ca++ Antagonist, HA1004; Pharmacological Properties Different From those of Nicardipine, J. Pharmacol. Exp. Ther., vol. 233, 1985, pp. 454–458.

T. Asano, Mechanism of Action of A Novel Antivasospasm Drug, HA1077, J. Pharmacol. Exp. Ther., vol. 241, 1987, pp. 1033–1040.

T. Asano et al., Vasodilator Actions of HA1077 in Vitro and in Vivo Putatively Mediated by The Inhibition of Protein Kinase, Br. J. Pharmacol., vol. 98, 1989, pp. 1091–1100.

T. Asano et al., New Pharmacological Strategies in Vasular Diseases: A Novel Intracellular Calsium Antagonist, HA1077 (AT–877) and Cerebral Vasospasm, Meth. Find. Exp. Clin. Pharmacol., vol. 12, 1990, pp. 443–448.

T. Asano et al., Blockade of Intracellular Actions of Calcium May Protect Against Ischaemic Damage to The Gerbil Brain, br. J. Pharmacol., vol. 103, 1991, pp. 1935–1938.

Manabu Shirotani et al., A New Type of Vasodilator, HA1077, An Isoquinoline Derivative, Inhibits Proliferation of Bovine Vascular Smooth Muscle Cells in Culture, J. Pharmacol. Exp. Thor. vol. 259, 1991, pp. 738–744.

Minoru Seto et al., Effects of HA1077, A Protein Kinase Inhibitor, on Myosin Phosphorylation and Tension in Smooth Muscle, Eur. J. Pharmacol., vol. 195, 1991, pp. 267–272.

Kazuhiro Sako et al., HA1077, A Novel Calcium Antagonistic Antivasospasm Drug, Increases Both Cerebral Blood Flow and Glucose Metabolism in Conscious Rats, Eur. J. Pharmacol., vol. 209, 1991, pp. 39–43.

Sh. Satoh et al., The Effects of HA1077 on The Cerebral Circulation After Subarachnoid Haemorrhage in Dogs, Acta Neurochir (Wein), vol. 110, 1991, pp. 185–188.

Kekkan (Blood Vessel), vol. 13, 1990, pp. 199–204.

*Primary Examiner*—Zohreh Fay
*Attorney, Agent, or Firm*—Finnegan, Henderson, Farabow, Garrett & Dunner, L.L.P.

[57] ABSTRACT

Disclosed is a cardio-protective agent for use in prophylaxis and treatment of myocardial disease and/or myocardial cell injury, which comprises an isoquinolinesulfonamide derivative represented by the following formula or a pharmaceutically acceptable acid addition salt thereof

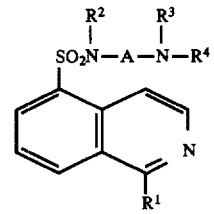

wherein $R^1$ represents H, Cl or OH; each of A, $R^2$, $R^3$ and $R^4$ is selected depending on the type of $R^1$, wherein A represents $C_2$–$C_6$ alkylene, which is optionally substituted with $C_1$–$C_{10}$ alkyl, cinnamyl, phenyl or benzyl, $R^2$ represents H or cycloalkyl having 6 carbon atoms or less, $R^3$ represents H, straight or branched $C_1$–$C_6$ alkyl, cinnamyl, phenyl or benzyl, or $R_2$ and $R_3$ together form alkylene having 4 carbon atoms or less, which is optionally substituted with $C_1$–$C_{10}$ alkyl, phenyl or benzoyl; and $R^4$ represents H, straight or branched $C_1$–$C_6$ alkyl, phenyl, benzyl, benzoyl, cinnamyl, cinnamoyl, furoyl,

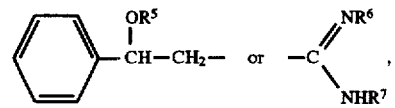

or $R^3$ and $R^4$ together with a neighboring nitrogen atom form 5 or 6-membered heterocyclic group, which optionally contains an oxygen atom; $R^5$ represents straight or branched $C_1$–$C_6$ alkyl; each of $R^6$ and $R^7$ is selected depending on the type of $R^1$, wherein each of $R^6$ and $R^7$ independently represents H or $CH_3$, or $R^6$ and $R^7$ together form $C_2$–$C_4$ alkylene.

12 Claims, No Drawings

CARDIO-PROTECTIVE AGENT

BACKGROUND OF THE INVENTION

1. Technical Field

The present invention relates to a novel use of an isoquinolinesulfonamide derivative. More particularly, the present invention is concerned with a cardio-protective agent comprising, as an active ingredient, a specific isoquinolinesulfonamide derivative or an acid addition salt thereof.

In the present invention, the term "cardio-protective agent" is intended to mean an agent which is effective for protecting a heart, specifically, and more particularly effective for prophylaxis and treatment of a myocardial disease and/or myocardial cell injury. Myocardial diseases and/or myocardial cell injury, which is caused by the influence of, for example, ischemia, ischemia/reperfusion or open heart surgery, finally results in the necrosis of myocardial cells. When the cardio-protective agent of the present invention is administered to a patient suffering from a myocardial disease and/or myocardial cell injury, the agent directly acts on the myocardial cells of the patient to prevent the necrosis of the myocardial cells. Accordingly, the cardio-protective agent of the present invention can be effectively used for prophylaxis and treatment of not only myocardial diseases, such as myocardial infarction and complications of myocardial infarction (e.g., shock, arrhythmia and heart failure, which accompany myocardial infarction), but also myocardial cell injury which is caused by ischemia/reperfusion in the treatment of myocardial infarction, such as thrombolytic therapy, percutaneous transluminal coronary angioplasty or the like, or which is caused by an arterial blocking or a sudden change in hemodynamics during or after open heart surgery.

2. Background Art

Heretofore, agents exhibiting cardio-protective activity have not yet been known which can be comprehensively, effectively used for prophylaxis and treatment of not only myocardial diseases, such as myocardial infarction and complications of myocardial infarction, but also myocardial cell injury which is caused by ischemia/reperfusion, open heart surgery or the like.

As conventional agents for the prophylaxis and treatment of myocardial diseases, such as myocardial infarction and complications of myocardial infarction (e.g., shock, arrhythmia and heart failure, which accompany myocardial infarction), there can be mentioned, for example, a nitrate-type agent having a vasodilative effect, such as nitroglycerin; a calcium channel blocker having a vasodilative effect, such as nifedipine, verapamil or diltiazem; and a β-blocker, such as atenolol. However, the therapeutic effects of these conventional agents for myocardial diseases are not satisfactory. On the other hand, as conventional agents for the prophylaxis and treatment of myocardial cell injury which is caused by ischemia/reperfusion in the treatment of myocardial infarction, such as thrombolytic therapy and percutaneous transluminal coronary angioplasty, there can be mentioned, for example, thrombolytic agents, such as urokinase and TPA (Tissue Plasminogen Activator). However, the therapeutic effects of these agents for myocardial cell injury are also not satisfactory. Thus, it has been conventional practice to use various different types of different agents selected depending on the conditions of patients suffering from a myocardial disease and/or myocardial cell injury, and agents, which can be comprehensively, effectively used for prophylaxis and treatment of a myocardial disease and myocardial cell injury, have not yet been known.

The above-mentioned diltiazem as a calcium channel blocker has a vasodilative effect and, therefore, has been used for prophylaxis and treatment of myocardial diseases, such as myocardial infarction. However, when diltiazem is administered to a patient, there is a danger of serious side effects such that the atrioventricular conducting system of the patient is depressed, leading to a decrease in heart rate. Also, other conventional agents as mentioned above are not free from the danger of side effects as well. Therefore, the above conventional agents do not satisfy the demand of clinicians.

In these situations, it has been desired to develop an agent which exhibits excellent cardio-protective effects with less side effects, so that it is effective for prophylaxis and treatment of a myocardial disease and/or myocardial cell injury.

SUMMARY OF THE INVENTION

The present inventors have made intensive and extensive studies with a view toward developing an agent which is effective for prophylaxis and treatment of myocardial disease and/or myocardial cell injury. As a result, it has unexpectedly been found that a specific isoquinolinesulfonamide derivative, e.g., 1-(5-isoquinolinesulfonyl) homopiperazine, which has conventionally been used as an antianginal agent or the like, is effective for prophylaxis and treatment of myocardial disease and/or myocardial cell injury, and has no side effect on the heart.

Conventionally, it is known that certain isoquinolinesulfonamides have a relaxing effect on vascular smooth muscle, an increasing effect on blood flow, an antihypertensive effect and a cerebral protective effect, so that it can be effectively used as a vasodilator, a cerebral circulation ameliorator, an antianginal agent, an antihypertensive agent, an agent for the prophylaxis and treatment of cerebrovascular and cardiovascular thrombosis, and an activator of cerebral metabolism.

Such isoquinolinesulfonamide derivatives are disclosed in, for example, Unexamined Japanese Patent Application Laid-Open Specification No. 57-156463 (corresponding to U.S. Pat. No. 4,456,757), Unexamined Japanese Patent Application Laid-Open Specification No. 57-200366 (corresponding to U.S. Pat. No. 4,560,755), and Unexamined Japanese Patent Application Laid-Open Specification Nos. 58-121278 and 58-121279 (both corresponding to U.S. Pat. No. 4,525,589).

More specifically, it has been reported that isoquinolinesulfonamide derivatives, such as 1-(5-isoquinolinesulfonyl) homopiperazine and 1-(1-hydroxy-5-isoquinolinesulfonyl) homopiperazine, have a relaxing effect on vascular smooth muscle, an increasing effect on blood flow, an antihypertensive effect and a cerebral protective effect and the like [see, for example, Unexamined Japanese Patent Application Laid-Open Specification Nos. 61-152658 and 61-227581 (both corresponding to U.S. Pat. No. 4,678,783); Unexamined Japanese Patent Application Laid-Open Specification No. 2-256617; J. Pharmacol. Exp. Ther., Vol. 241, 1033 (1987); Br. J. Pharmacol., Vol. 98, 1091 (1989); Kekkan (Blood Vessel), Vol. 13, 199 (1990); Meth. Find Exp. Cln. Pharmacol., Vol. 12, 443 (1990); Br. J. pharmacol., Vol. 103, 1935 (1991); J. Pharmacol. Exp. Ther., Vol. 259, 738 (1991); Eur. J. Pharmacol., Vol. 195, 267 (1991); Eur. J. Pharmacol. Vol. 209, 39 (1991); and Acta Neurochir., Vol. 110, 185 (1991)].

The working examples of the above-mentioned U.S. Pat. No. 4,678,783 demonstrate the effects of the isoquinolinesulfonamide derivatives on the isolated superior mesenteric artery in a rabbit, the blood flow of the canine femoral artery and canine vertebral artery, and the blood pressure of a spontaneous hypertensive rat. The working examples of the above-mentioned Unexamined Japanese Patent Application Laid-Open Specification No. 2-256617 demonstrate the effects of the isoquinolinesulfonamide derivatives on the respiratory rate in brain mitochondria, the brain injury in a hypoxic mouse, and the delayed neuronal death of the hippocampus in a Mongolian gerbil. The above-mentioned J. Pharmacol. Exp. Ther., Vol. 259, 738 (1991) demonstrates the effects of the isoquinolinesulfonamide derivatives on the proliferation of smooth muscle. From the above prior art references, it can be seen that isoquinolinesulfonamide derivatives have various effects on blood vessels, such as a relaxing effect on vascular smooth muscle.

It has also been reported that isoquinolinesulfonamide derivatives, such as N-(2-guanidinoethyl)-5-isoquinolinesulfonamide, have a relaxing effect on vascular smooth muscle and an increasing effect on blood flow [see Unexamined Japanese Patent Application Laid-Open Specification Nos. 59-93054 and 60-81168, (both corresponding to U.S. Pat. No. 4,634,770); J. Pharmacol. Exp. Ther., Vol. 231, 141 (1984); and J. Pharmacol. Exp. Ther., Vol. 233, 454 (1985)].

However, all of the above-mentioned patent documents and papers only teach the effects of isoquinolinesulfonamide derivatives on organs other than myocardium, such as blood vessels and cerebral tissues, and do not teach or suggest that isoquinolinesulfonamide derivatives directly act on myocardial cells to thereby exhibit an excellent cardio-protective effect.

It is known that myocardial diseases, such as myocardial infarction and the like, are pathologically, fundamentally, different from angina pectoris [see "Kyoshinsho (angina pectoris)", 85–105 (1978), published by Kanahara & Co., Ltd., Japan; and "Igaku Kakuron Memorandamu (Memorandum on Special Medicine) 3" 'Shinzou Myakukan shikkan (Cardiac and Vasal Diseases)', 94–108 and 220–228 (1990), published by Bunkodo Co., Ltd., Japan]. Therefore, it is not necessarily likely that an agent which can be effectively used for the treatment of angina pectoris can also be effectively, safely used for treatment of myocardial diseases. For example, as mentioned above, diltiazem has a vasodilative effect and has been used as an antianginal agent. However, it is known that diltiazem causes undesirable side effects on the heart, e.g., decrease in heart rate. Therefore, diltiazem cannot be used as an agent for the treatment of myocardial diseases, such as myocardial infarction.

From the above fact that diltiazem causes undesirable side effects on the heart, it is unexpected and surprising that isoquinolinesulfonamide derivatives, which, like diltiazem, have been used as antianginal agents exhibit no side effect on the heart, and are effective for prophylaxis and treatment of a myocardial disease and/or myocardial cell injury.

Illustratively stated, it has unexpectedly been found that when endothelin (which causes myocardial infarction) is administered to a rabbit after administration of an isoquinolinesulfonamide derivative to the rabbit, crisis of myocardial infarction can be remarkably inhibited. Further, when the heart is taken out from a rat and ischemia/reperfusion of the isolated heart is performed, myocardial cell injury is immediately induced. However, it has unexpectedly been found that when physiological saline containing an isoquinolinesulfonamide derivative is added to the perfusion solution and reperfusion is performed after the ischemia, the myocardial cell injury is drastically inhibited.

The present invention has been completed, based on these novel findings.

Accordingly, it is an object of the present invention to provide a novel cardio-protective agent, which is not only effective for prophylaxis and treatment of myocardial disease and/or myocardial cell injury, but also has extremely little side effect.

In one aspect of the present invention, there is provided a cardio-protective agent for use in prophylaxis and treatment of myocardial disease and/or myocardial cell injury, which comprises an effective amount of an isoquinolinesulfonamide derivative represented by formula (I) or a pharmaceutically acceptable acid addition salt thereof

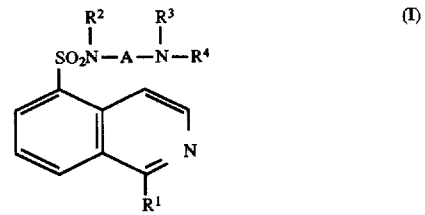

wherein $R^1$ represents a hydrogen atom, a chlorine atom or a hydroxyl group, and wherein:

when $R^1$ is a hydrogen atom, A represents a $C_2$–$C_6$ alkylene group, which is unsubstituted or substituted with at least one substituent selected from the group consisting of a $C_1$–$C_{10}$ alkyl group, a cinnamyl group, a phenyl group and a benzyl group; $R^2$ represents a hydrogen atom or a cycloalkyl group having 6 carbon atoms or less; $R^3$ represents a hydrogen atom, a straight or branched $C_1$–$C_6$ alkyl group, a cinnamyl group, a phenyl group or a benzyl group; or $R^2$ and $R^3$ together form an alkylene group having 4 carbon atoms or less, which is unsubstituted or substituted with at least one substituent selected from the group consisting of a $C_1$–$C_{10}$ alkyl group, a phenyl group and a benzoyl group; and $R^4$ represents a hydrogen atom, a straight or branched $C_1$–$C_6$ alkyl group, a phenyl group, a benzyl group, a benzoyl group, a cinnamyl group, a cinnamoyl group, a furoyl group, a group represented by the formula:

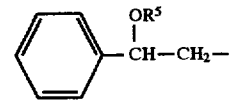

wherein $R^5$ represents a straight or branched $C_1$–$C_6$ alkyl group, or an amidino group represented by the formula:

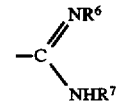

wherein each of $R^6$ and $R^7$ independently represents a hydrogen atom or a methyl group, or $R^6$ and $R^7$ together form a $C_2$–$C_4$ alkylene group;

or $R^3$ and $R^4$ together with a neighboring nitrogen atom form a 5 or 6-membered heterocyclic group, which group optionally contains an oxygen atom; and when $R^1$ is a chlorine atom or a hydroxyl group, A represents a $C_2$–$C_6$ alkylene group, which is unsubstituted or substituted with at least one $C_1$–$C_6$ alkyl group; each of $R^2$ and $R^3$ independently represents a hydrogen atom, a straight or branched $C_1$–$C_6$ alkyl group or a cycloalkyl group having 6 carbon atoms or less, or $R^2$ and $R^3$ together form an ethylene or a trimethylene group, which is unsubstituted or substituted with at least one $C_1$–$C_6$ alkyl group; and $R^4$ represents a hydrogen atom, a $C_1$–$C_6$ alkyl group or an amidino group represented by the formula:

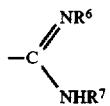

wherein each of $R^6$ and $R^7$ independently represents a hydrogen atom or a methyl group.

In another aspect of the present invention, there is provided a method for the prophylaxis and treatment of myocardial disease and/or myocardial cell injury, which comprises administering to a patient suffering from myocardial disease and/or myocardial cell injury, or a living body diagnosed to be susceptible to myocardial disease and/or myocardial cell injury an effective amount of an isoquinolinesulfonamide derivative represented by formula (I) or a pharmaceutically acceptable acid addition salt thereof.

In formula (I), it is preferred that $R_1$ be a hydrogen atom or a hydroxyl group. When $R_1$ is a hydrogen atom, it is preferred that A be an ethylene group or a trimethylene group, that $R_2$ and $R_3$ together form a trimethylene group when A is an ethylene group or form an ethylene group when A is a trimethylene group, and that $R_4$ be a hydrogen atom.

When $R_1$ is a hydroxyl group, it is preferred that A be an ethylene group or a trimethylene group, $R_2$ and $R_3$ together form a trimethylene group when A is an ethylene group or form an ethylene group when A is a trimethylene group, and that $R_4$ be a hydrogen atom.

Specific examples of isoquinolinesulfonamide derivatives represented by formula (I) of the present invention include the following compounds:

(1) 1-(5-isoquinolinesulfonyl)homopiperazine
(2) 1-(5-isoquinolinesulfonyl)-2-methylhomopiperazine;
(3) 1-(5-isoquinolinesulfonyl)-3-methylhomopiperazine;
(4) 1-(5-isoquinolinesulfonyl)-6-methylhomopiperazine;
(5) 1-(5-isoquinolinesulfonyl)-2,3-dimethylhomopiperazine;
(6) 1-(5-isoquinolinesulfonyl)-3,3-dimethylhomopiperazine;
(7) 1-(5-isoquinolinesulfonyl)-3-ethylhomopiperazine;
(8) 1-(5-isoquinolinesulfonyl)-3-propylhomopiperazine;
(9) 1-(5-isoquinolinesulfonyl)-3-isobutylhomopiperazine;
(10) 1-(5-isoquinolinesulfonyl)-3-phenylhomopiperazine;
(11) 1-(5-isoquinolinesulfonyl)-3-benzylhomopiperazine;
(12) 1-(5-isoquinolinesulfonyl)-6-ethylhomopiperazine;
(13) 1-(5-isoquinolinesulfonyl)-6-propylhomopiperazine;
(14) 1-(5-isoquinolinesulfonyl)-6-butylhomopiperazine;
(15) 1-(5-isoquinolinesulfonyl)-6-pentylhomopiperazine;
(16) 1-(5-isoquinolinesulfonyl)-6-hexylhomopiperazine;
(17) 1-(5-isoquinolinesulfonyl)-6-phenylhomopiperazine;
(18) 1-(5-isoquinolinesulfonyl)-6-benzylhomopiperazine;
(19) 1-(5-isoquinolinesulfonyl)-4-methylhomopiperazine;
(20) 1-(5-isoquinolinesulfonyl)-4-ethylhomopiperazine;
(21) 1-(5-isoquinolinesulfonyl)-4-propylhomopiperazine;
(22) 1-(5-isoquinolinesulfonyl)-4-butylhomopiperazine;
(23) 1-(5-isoquinolinesulfonyl)-4-hexylhomopiperazine;
(24) N-(2-aminoethyl)-1-chloro-5-isoquinolinesulfonamide;
(25) N-(4-aminobutyl)-1-chloro-5-isoquinolinesulfonamide;
(26) N-(2-amino-1-methylethyl)-1-chloro-5-isoquinolinesulfonamide;
(27) N-(2-amino-1-methylpentyl)-1-chloro-5-isoquinolinesulfonamide;
(28) N-(3-amino-2-methylbutyl)-1-chloro-5-isoquinolinesulfonamide;
(29) N-(3-di-n-butylaminopropyl)-1-chloro-5-isoquinolinesulfonamide;
(30) N-(N-cyclohexyl-N-methylaminoethyl)-1-chloro-5-isoquinolinesulfonamide;
(31) N-(2-guanidinoethyl)-1-chloro-5-isoquinolinesulfonamide;
(32) N-(4-guanidinobutyl)-1-chloro-5-isoquinolinesulfonamide;
(33) N-(2-guanidino-1-methylethyl)-1-chloro-5-isoquinolinesulfonamide;
(34) N-(1-guanidinomethylpentyl)-1-chloro-5-isoquinolinesulfonamide;
(35) N-(2-guanidino-3-methylbutyl)-1-chloro-5-isoquinolinesulfonamide;
(36) N-(3-guanidino-2-methylpropyl)-1-chloro-5-isoquinolinesulfonamide;
(37) N-(4-guanidino-3-methylbutyl)-1-chloro-5-isoquinolinesulfonamide;
(38) 2-methyl-4-(1-chloro-5-isoquinolinesulfonyl)piperazine;
(39) 2-ethyl-4-(1-chloro-5-isoquinolinesulfonyl)piperazine;
(40) 2-isobutyl-4-(1-chloro-5-isoquinolinesulfonyl)piperazine;
(41) 2,5-dimethyl-4-(1-chloro-5-isoquinolinesulfonyl)piperazine;
(42) 1-methyl-4-(1-chloro-5-isoquinolinesulfonyl)piperazine;
(43) 1-amidino-4-(1-chloro-5-isoquinolinesulfonyl)piperazine;
(44) 1-amidino-4-(1-chloro-5-isoquinolinesulfonyl)homopiperazine;
(45) 1-amidino-3-methyl-4-(1-chloro-5-isoquinolinesulfonyl)piperazine;
(46) 1-amidino-2,5-dimethyl-4-(1-chloro-5-isoquinolinesulfonyl)piperazine;
(47) N-(2-aminoethyl)-1-hydroxy-5-isoquinolinesulfonamide;
(48) N-(4-aminobutyl)-1-hydroxy-5-isoquinolinesulfonamide;
(49) N-(2-amino-1-methylethyl)-1-hydroxy-5-isoquinolinesulfonamide;
(50) N-(2-amino-1-methylheptyl)-1-hydroxy-5-isoquinolinesulfonamide;
(51) N-(3-amino-2-methylbutyl)-1-hydroxy-5-isoquinolinesulfonamide;
(52) N-[3-(N,N-dibutylamino)propyl]-1-hydroxy-5-isoquinolinesulfonamide;
(53) N-[2-(N-cyclohexyl-N-methylamino)ethyl]-1-hydroxy-5-isoquinolinesulfonamide;
(54) N-(2-guanidinoethyl)-1-hydroxy-5-isoquinolinesulfonamide;
(55) N-(4-guanidinobutyl)-1-hydroxy-5-isoquinolinesulfonamide;
(56) N-(2-guanidino-1-methylethyl)-1-hydroxy-5-isoquinolinesulfonamide;
(57) N-(1-guanidinomethylpentyl)-1-hydroxy-5-isoquinolinesulfonamide;

(58) N-(2-guanidino-3-methylbutyl)-1-hydroxy-5-isoquinolinesulfonamide;
(59) N-(3-guanidino-2-methylpropyl)-1-hydroxy-5-isoquinolinesulfonamide;
(60) N-(4-guanidino-3-methylbutyl)-1-hydroxy-5-isoquinolinesulfonamide;
(61) 2-methyl-4-(1-hydroxy-5-isoquinolinesulfonyl)piperazine;
(62) 2-ethyl-4-(1-hydroxy-5-isoquinolinesulfonyl)piperazine;
(63) 2-isobutyl-4-(1-hydroxy-5-isoquinolinesulfonyl)piperazine;
(64) 2,5-dimethyl-4-(1-hydroxy-5-isoquinolinesulfonyl)piperazine;
(65) 1-methyl-4-(1-hydroxy-5-isoquinolinesulfonyl)piperazine;
(66) 1-amidino-4-(1-hydroxy-5-isoquinolinesulfonyl)piperazine;
(67) 1-amidino-4-(1-hydroxy-5-isoquinolinesulfonyl)homopiperazine;
(68) 1-amidino-3-methyl-4-(1-hydroxy-5-isoquinolinesulfonyl)piperazine;
(69) 1-amidino-2,5-dimethyl-4-(1-hydroxy-5-isoquinolinesulfonyl)piperazine;
(70) N-(2-methylaminoethyl)-1-chloro-5-isoquinolinesulfonamide;
(71) N-(2-ethylaminoethyl)-1-chloro-5-isoquinolinesulfonamide;
(72) N-(2-propylaminoethyl)-1-chloro-5-isoquinolinesulfonamide;
(73) N-(2-butylaminoethyl)-1-chloro-5-isoquinolinesulfonamide;
(74) N-(2-hexylaminoethyl)-1-chloro-5-isoquinolinesulfonamide;
(75) 1-(1-chloro-5-isoquinolinesulfonyl)piperazine;
(76) 1-(1-chloro-5-isoquinolinesulfonyl)homopiperazine;
(77) N-(2-methylaminoethyl)-1-hydroxy-5-isoquinolinesulfonamide;
(78) N-(2-ethylaminoethyl)-1-hydroxy-5-isoquinolinesulfonamide;
(79) N-(2-propylaminoethyl)-1-hydroxy-5-isoquinolinesulfonamide;
(80) N-(2-butylaminoethyl)-1-hydroxy-5-isoquinolinesulfonamide;
(81) N-(2-hexylaminoethyl)-1-hydroxy-5-isoquinolinesulfonamide;
(82) 1-(1-hydroxy-5-isoquinolinesulfonyl)piperazine;
(83) 1-(1-hydroxy-5-isoquinolinesulfonyl)homopiperazine;
(84) 1-(5-isoquinolinesulfonyl)-4-methylpiperazine;
(85) 1-(5-isoquinolinesulfonyl)-4-n-hexylpiperazine;
(86) 1-(5-isoquinolinesulfonyl)-4-cinnamylpiperazine;
(87) 1-(5-isoquinolinesulfonyl)piperazine;
(88) N-(2-aminoethyl)-5-isoquinolinesulfonamide;
(89) N-(4-aminobutyl)-5-isoquinolinesulfonamide;
(90) N-(3-di-n-butylaminopropyl)-5-isoquinolinesulfonamide;
(91) 1-(5-isoquinolinesulfonyl)-3-methylpiperazine;
(92) 1-(5-isoquinolinesulfonyl)-3-isobutylpiperazine;
(93) 1-(5-isoquinolinesulfonyl)-2,5-dimethylpiperazine;
(94) N-(3-guanidino-2-phenylpropyl)-5-isoquinolinesulfonamide;
(95) N-(6-guanidino-1-methylheptyl)-5-isoquinolinesulfonamide;
(96) 2-[2-(5-isoquinolinesulfonamide)ethylamino]-2-imidazoline;
(97) 2-amidino-1-(5-isoquinolinesulfonyl)piperazine;
(98) 4-amidino-2,5-dimethyl-1-(5-isoquinolinesulfonyl)piperazine;
(99) 4-amidino-1-(5-isoquinolinesulfonyl)homopiperazine;
(100) 4-($N^1,N^2$-dimethylamino)-1-(5-isoquinolinesulfonyl)piperazine;
(101) 4-amidino-3-butyl-1-(5-isoquinolinesulfonyl)piperazine;
(102) 4-hexyl-1-(5-isoquinolinesulfonyl)ethylenediamine;
(103) N-(4-guanidinobutyl)-5-isoquinolinesulfonamide; and
(104) N-(2-guanidinoethyl)-5-isoquinolinesulfonamide.

In the present invention, as an active ingredient for a cardio-protective agent, not only the isoquinolinesulfonamide derivative represented by formula (I), but also an acid addition salt thereof can be used. This salt is a pharmaceutically acceptable, non-toxic salt. Examples of acid addition salts of the isoquinolinesulfonamide derivative (I) include salts with inorganic acids, such as hydrochloric acid, hydrobromic acid, phosphoric acid and sulfuric acid, and salts with organic acids, such as acetic acid, citric acid, tartaric acid, lactic acid, succinic acid, fumaric acid, maleic acid and methanesulfonic acid.

There is no particular limitation with respect to the method for producing the isoquinolinesulfonamide derivative represented by formula (I), and it can be produced by various methods. With respect to the production methods, reference can be made to, for example, the methods disclosed in Unexamined Japanese Patent Application Laid-Open Specification No. 61-152658 and Unexamined Japanese Patent Application Laid-Open Specification No. 61-227581 (corresponding to U.S. Pat. No. 4,678,783), Unexamined Japanese Patent Application Laid-Open Specification No. 57-156463 (corresponding to U.S. Pat. No. 4,456,757), Unexamined Japanese Patent Application Laid-Open Specification No. 57-200366 (corresponding to U.S. Pat. No. 4,560,755), Unexamined Japanese Patent Application Laid-Open Specification No. 58-121278 and Unexamined Japanese Patent Application Laid-Open Specification No. 58-121279 (corresponding to U.S. Pat. No. 4,525,589), Unexamined Japanese Patent Application Laid-Open Specification No. 59-93054 and Unexamined Japanese Patent Application Laid-Open Specification No. 60-81168 (corresponding to U.S. Pat. No. 4,634,770).

For example, 1-(5-isoquinolinesulfonyl)homopiperazine represented by formula (IV) can be obtained by reacting 5-isoquinolinesulfonic acid chloride represented by formula (V) with homopiperazine represented by formula (VI), in accordance with the following reaction scheme.

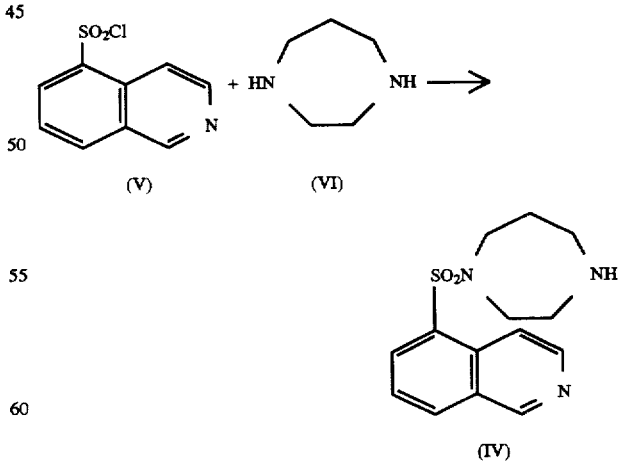

The above reaction can be effected in accordance with the method described in U.S. Pat. No. 4,676,783.

The acid addition salt of the isoquinolinesulfonamide derivative can be readily prepared by reacting the above isoquinolinesulfonamide derivative with an inorganic acid or an organic acid. On the other hand, when the desired compound is obtained in the form of an acid addition salt, the corresponding compound in free form can be easily formed by treating the salt with alkali.

The isoquinolinesulfonamide derivative represented by formula (I) or the acid addition salt thereof can be administered as such or in the form of a composition with a pharmaceutically acceptable carrier, diluent or excipient. With respect to such a composition, the proportion of each component can be appropriately determined in accordance with the manner or scheme of administration.

The isoquinolinesulfonamide derivative represented by formula (I) may be used in combination with other medicines, depending on the symptoms of the patient.

When the isoquinolinesulfonamide derivative represented by formula (I) is orally administered, it can be employed in various forms, such as tablet, capsule, powder, granule, liquid preparation and elixir. When the above isoquinolinesulfonamide derivative is parenterally administered, it can also be employed in various forms, such as an agent for injection, suppository, ointment and nasal drop.

Examples of solid carriers to be used for oral administration of the isoquinolinesulfonamide derivative include oligosaccharide, such as lactose, refined sugar and mannitol; starch, such as corn and potato; excipients, such as crystalline cellulose, calcium phosphate and synthetic aluminum silicate; sodium salt or calcium salt of carboxymethyl cellulose; fatty acid salt, such as magnesium stearate; talc; processed starch, such as hydroxypropyl methyl cellulose and methyl cellulose; gelatin, agar, gum and sodium alginate; and polyethylene glycol.

When the isoquinolinesulfonamide derivative is employed in the form of a capsule, tablet, granule and powder, the content of the isoquinolinesulfonamide derivative as active ingredient generally is from 1 to 80% by weight, preferably from 1 to 60% by weight.

When the isoquinolinesulfonamide derivative is orally administered in the form of a liquid preparation, it is preferred that the liquid preparation be a solution or syrup containing from 0.01 to 20% by weight of the isoquinolinesulfonamide derivative as an active ingredient. In this case, it is preferred that the carrier to be used contain an aromatic agent or a sweetening agent in addition to water and ethanol.

When the isoquinolinesulfonamide derivative is parenterally administered by way of intramuscular injection, intravenous injection or subcutaneous injection, the isoquinolinesulfonamide derivative represented by formula (I) as an active ingredient is formulated into a sterilized solution which is rendered isotonic by the addition of other solute, such as salt and glucose.

Examples of suitable solvents for preparing liquid preparations for injection include sterilized water, solution of lidocaine hydrochloride (for intramuscular injection), physiological saline, glucose, liquid preparation for intravenous injection and electrolytic solution (for intravenous injection). It is preferred that the above-mentioned liquid preparations contain generally from 0.01 to 20% by weight, preferably from 0.1 to 10% by weight of the isoquinolinesulfonamide derivative as an active ingredient.

When the isoquinolinesulfonamide derivative is administered in the form of a suppository or ointment (percutaneous agent), it is preferred that the isoquinolinesulfonamide derivative as an active ingredient be contained in an amount of from 1 to 80% by weight. In this case, examples of carriers which can be used include oils and fats derived from animals and plants, such as vaseline, paraffin, yellow wax, lanolin and cacao butter; synthetic oils and fats, such as macrogol and witepsol; emulsifier; preservative; and absorption accelerator can be used.

When a preparation for nasal administration having the isoquinolinesulfonamide derivative as an active ingredient is made, additives, such as an emulsifier and other accelerating agents (e.g., absorption accelerator), can be used in addition to the above-mentioned carriers used for liquid preparations.

The dose of the isoquinolinesulfonamide derivative represented by formula (I) is varied depending on the age, condition of health, weight and condition of the patient, and the type of medical treatment if the patient has simultaneously another treatment, frequency of the treatment, nature of desired effect etc. However, the dose may generally be in the range of from 0.01 to 40 mg/kg (weight) per day. When the isoquinolinesulfonamide derivative is orally administered, it is preferred that the dose be from 0.02 to 40 mg/kg (weight) per day, and in the case of parenteral administration, it is preferred that the dose be from 0.01 to 20 mg/kg (weight) per day. The daily dose may be administered at one time, or it may be divided into several portions and these portions administered at intervals. In the case of intravenous administration, parenteral solution for injection comprising the isoquinolinesulfonamide derivative represented by formula (I) can be administered, for example, taking 30 to 60 minutes at one time.

As clearly shown in the following Examples, the cardio-protective agent of the present invention is effective for the prophylaxis and therapy of myocardial disease and/or myocardial cell injury.

BEST MODE FOR CARRYING OUT THE INVENTION

The present invention will be described in greater detail with reference to the following Examples, which should not be construed as limiting the scope of the present invention.

EXAMPLE 1

Inhibitory effect on endothelin-induced myocardial infarction

The inhibitory effect of the cardio-protective agent of the present invention on endothelin-induced myocardial infarction was examined in the following manner.

The animals used in the examination were Japanese White rabbits each weighing 2.0 to 3.1 kg, which were divided into two groups, i.e., a first group consisting of 40 rabbits and a second group consisting of 13 rabbits. The hydrochloride of the above-mentioned compound (1) was dissolved in distilled water, and the resultant solution was orally administered to each of 10 rabbits of the first group in an amount of 3.0 mg/kg (body weight). In the same manner as mentioned above, diltiazem and nicorandil were individually, orally administered to each of another 10 rabbits of the first group. As a control, distilled water was orally administered to each of the remaining 10 rabbits of the first group.

With respect to the rabbits of the second group, the above-prepared aqueous solution of the hydrochloride of compound (1) was orally administered to each of 7 rabbits in the same manner as mentioned above, and as a control, distilled water was orally administered to each of the remaining 6 rabbits.

Fifteen minutes after the administration, 1.2 nmol/kg (body weight) of endothelin (manufactured and sold by Peptide Institute, Japan) was injected into the auricular vein of each of the above rabbits of the first and second groups, thereby inducing myocardial infarction. With respect to the rabbits of the first and second groups, the degree of myocardial infarction was evaluated by rabbit electrocardiogram and by measuring the activity of enzymes leaked into the rabbit plasma, respectively, as follows.

With respect to each of the rabbits of the first group, the rabbit electrocardiogram was taken just before and 3 minutes after the injection of endothelin, according to the standard limb lead II induction method [Ozawa, Training of Electrocardiogram. p. 24–32, 1984, Chugai Igaku Co., Ltd., Japan), and T-wave elevation was measured. Results are shown in Table 1.

TABLE 1

| Test agents | Dose [mg/kg (body weight)] | Number of rabbits | T-wave elevation* (mV) |
|---|---|---|---|
| Distilled water | | 10 | 0.63 |
| Hydrochloride of compound (1) | 3.0 | 10 | 0.00 |
| Diltiazem | 3.0 | 10 | 0.46 |
| Nicorandil | 3.0 | 10 | 0.58 |

Note
*: T-wave elevation data shown are mean values.

As shown in Table 1, with respect to the rabbits to which distilled water alone was administered, drastic T-wave elevation was observed, whereas with respect to the rabbits to which the hydrochloride of compound (1) was administered, T-wave elevation was 0 mV. That is, the hydrochloride of compound (1) can remarkably inhibit the T-wave elevation. With respect to the rabbits to which diltiazem or nicorandil was administered as a comparative agent, T-wave elevation was not inhibited.

With respect to each of the rabbits of the second group, the blood was collected using a heparinized syringe just before and thirty minutes after the intravenous administration of endothelin. The collected blood was subjected to centrifugation using a cooling centrifuge (CR20B2, manufactured and sold by Hitachi Corp., Japan), to thereby separate plasma. With respect spect to the separated plasma, lactate dehydrogenase activity was measured by the UV method, and creatine kinase activity was measured by the GSCC method [method based on the suggestions of German Society of Clinical Chemistry; Anon. J. Clin. Chem. Clin. Biochem, vol. 15, 249 (1977); and Chemnitz. G., et al. Dtsch. med. Wschr, vol. 104, 257 (1979)]. The above measurements were conducted using CentrisiChem Encore (manufactured and sold by Baker Co., Ltd., U.S.A.). Results are shown in Table 2.

TABLE 2

| Test agents | Number of rabbits | Just before administration | 30 Min. after administration |
|---|---|---|---|
| | | Lactate dehydrogenase activity* (IU/l) | |
| Distilled water | 6 | 29.3 | 74.8 |
| Hydrochloride of compound (1) (3.0 mg/kg · weight) | 7 | 29.7 | 52.1 |
| | | Creatine kinase activity* (IU/l) | |
| Distilled water | 6 | 122.0 | 190.0 |
| Hydrochloride of compound (1) (3.0 mg/kg · weight) | 7 | 114.6 | 163.9 |

Note
*: The activity data shown are mean values.

As shown in Table 2, the hydrochloride of compound (1) had an inhibitory effect on the lactate dehydrogenase activity and creatine kinase activity in plasma, which activities were caused by the intravenous administration of endothelin.

From Tables 1 and 2 above, it has been confirmed that the isoquinolinesulfonamide derivative represented by formula (I) is effective for prophylaxis and treatment of myocardial infarction.

EXAMPLE 2

Inhibitory effect on myocardial cell injury caused by ischemia/reperfusion (1)

Hearts excised from male Wistar rats (approximately six-week old) were perfused with the Krebs-Heiseleit solution according to the Langendorff method [Tamura and Fujii, "Yakurigaku Jikkenho (Experimental Methods in Pharmacology)", pp. 176–177, 1990, published by Kyodoisho Publishing Co., Ltd., Japan; and Yamada, Kubota et al., "Yakurigaku Jisshu (Pharmacological Practice)", pp. 79–81, 1979, published by Kodansha Scientific Co., Ltd., Japan]. After the isolated hearts were allowed to stabilize, the flowing of the perfusate was temporarily stopped, and the isolated hearts were allowed to be in an ischemic state for 40 minutes. Subsequently, reperfusion was conducted for 40 minutes.

Hydrochlorides of compounds (1) and (83) mentioned above were individually dissolved in distilled water, and the resultant aqueous solutions of the hydrochlorides of compounds (1) and (83) were individually introduced to and perfused in a perfusion circuit with the reperfusate for 5 minutes simultaneously with the initiation of reperfusion. In the same manner as mentioned above, diltiazem as a comparative agent and physiological saline as a control were individually perfused with the reperfusate. The perfusion conditions of the aqueous solutions of the hydrochlorides of compounds (1) and (83), diltiazem and physiological saline are shown in Table 3.

With respect to each of the test agents, the coronary artery flow was measured just before the ischemia, i.e., the stopping of the perfusion, and 40 minutes after the initiation of reperfusion using an electromagnetic flow probe FF-030P (manufactured and sold by Nippon Koden Corp., Japan). Results are shown in Table 3.

TABLE 3

| Test agents | Concentration | Coronary flow change (% based on pre-ischemic values)* | Number of samples |
|---|---|---|---|
| Physiological saline | | 53% | 5 |
| Hydrochloride of compound (1) | $3 \times 10^{-6}M$ | 70% | 4 |
| Hydrochloride of compound (83) | $1 \times 10^{-5}M$ | 58% | 4 |
| | $3 \times 10^{-5}M$ | 61% | 4 |
| Diltiazem | $3 \times 10^{-6}M$ | 54% | 5 |
| | $1 \times 10^{-5}M$ | bradycardia and cardiac arrest | 3 |

Note
*: The percentages shown are ratios of the coronary artery flow measured 40 minutes after the initiation of reperfusion, relative to the coronary artery flow measured just before the ischemia.

As shown in Table 3, when physiological saline was perfused, the myocardial cell injury was drastically caused by the ischemia/reperfusion, whereas when the aqueous solutions of the hydrochlorides of compounds (1) and (83) were individually perfused, the lowering of coronary artery flow was greatly inhibited. When diltiazem was perfused, bradycardia and cardiac arrest occurred, whereas when the aqueous solutions of the hydrochlorides of compounds (1) and (83) were individually perfused, neither bradycardia nor cardiac arrest occurred. From the above, it has been confirmed that by the use of the isoquinolinesulfonamide derivative represented by formula (I), prophylaxis and treatment of the myocardial cell injury caused by ischemia/reperfusion are effected.

EXAMPLE 3

Inhibitory effect on myocardial cell injury caused by ischemia/reperfusion (2)

In the same manner as in Example 2, hearts excised from rats were perfused in the Krebs-Henseleit solution in accordance with the Langendorff method. After the isolated hearts were allowed to stabilize, the flowing of the perfusate was temporarily stopped, and the isolated hearts were allowed to be in an ischemic state for 20 minutes. Subsequently, reperfusion was conducted for 60 minutes. As activities of the leaked enzymes, the lactate dehydrogenase activity and creatine dehydrogenase activity were examined with respect to each of the samples using an autoanalizer (Super Z 818, manufactured and sold by NITTEC Co., Ltd., Japan). The aqueous solutions of the hydrochlorides of compounds (1) and (83) were individually introduced to and perfused in a perfusion circuit with reperfusate simultaneously with the initiation of the reperfusion under the conditions as shown in Table 4. As a control, physiological saline was perfused with the reperfusate in the same manner as mentioned above. The above-mentioned activities of the enzymes leaked into the perfusate and reperfusate were, respectively, measured before the ischemia and 10 minutes after the initiation of reperfusion. Results are shown in Table 4.

TABLE 4

| Test agents | Number of samples | Before ischemia | 10 Min. after initiation of reperfusion |
|---|---|---|---|
| | | Lactate dehydrogenase activity* (IU/min) | |
| Physiological saline | 6 | 33.3 | 984.3 |
| Hydrochloride of compound (1) | | | |
| $10^{-6}$M | 4 | 22.8 | 732.8 |
| $10^{-5}$M | 5 | 21.3 | 575.3 |
| Physiological saline | 4 | 25.0 | 1035.2 |
| Hydrochloride of compound (83) | | | |
| $10^{-5}$M | 5 | 1.2 | 487.0 |
| | | Creatine kinase activity* (IU/min) | |
| Physiological saline | 6 | 12.6 | 1588.1 |
| Hydrochloride of compound (1) | | | |
| $10^{-6}$M | 4 | 26.6 | 1159.8 |
| $10^{-5}$M | 5 | 18.6 | 901.5 |
| Physiological saline | 4 | 14.9 | 1329.5 |
| Hydrochloride of compound (83) | | | |
| $10^{-5}$M | 5 | 17.4 | 881.5 |

Note
*: The activity data shown are mean values

As shown in Table 4, when physiological saline was perfused, a drastic increase in activities of the leaked enzymes was observed. By contrast, when the aqueous solutions of the hydrochlorides of compounds (1) and (83) were individually perfused, the activities of the leaked enzymes were greatly inhibited. Because only the isolated hearts were used in the above experiments, it is demonstrated that the enzymes leaked into the reperfusate are those which are derived from the cardial cells. Accordingly, the results shown in Table 4 clearly indicate that the isoquinolinesulfonamide derivative represented by formula (I) directly acts on the myocardial cells to thereby effect prophylaxis and treatment of the myocardial cell injury.

EXAMPLE 4

Toxity in oral administration

Hydrochlorides of compounds (1) and (83) were individually dissolved in distilled water, and the resultant aqueous solutions were individually, orally administered to five Japanese White rabbits having a weight of about 3.0 kg in a dose as shown in Table 5, and whether the rabbits died or not was observed. Results are shown in Table 5.

TABLE 5

| Test agents | Dose [mg/kg (body weight)] | Number of rabbits died/ Number of rabbits tested |
|---|---|---|
| Hydrochloride of compound (1) | 30 | 0/5 |
| Hydrochloride of compound (83) | 30 | 0/5 |

As shown in Table 5, even when the isoquinolinesulfonamide derivative represented by formula (I) was orally administered in a dose which is 10 times as high as a therapeutically effective amount thereof, no rabbits died. From the above results, safety of the isoquinolinesulfonamide derivative has been confirmed.

EXAMPLE 5

Formulation Examples
(1) Tablet
A tablet containing the following components is prepared by a known method.

| Components | Formulation |
|---|---|
| Hydrochloride of compound (1) | 30 mg |
| Crystalline cellulose | 40 mg |
| Lactose | 103 mg |
| Magnesium stearate | 2 mg |
| Calcium carboxymethyl cellulose | 5 mg |
| Total | 180 mg |

(2) Sterilized solution for injection

The below-mentioned components are dissolved in a distilled water to obtain a solution. Distilled water is further added to the obtained solution to a desired volume. 2 ml of the resultant solution is placed into each of a predetermined number of ampules and sealed. The ampules are subjected to heat sterilization. The formulation of the components per ampule is as follows.

| Components | Formulation |
|---|---|
| Hydrochloride of compound (1) | 50 mg |
| Sodium chloride | 16 mg |
| Distilled water | An amount such that the volume of the final solution becomes 2 ml |

Industrial Applicability

The cardio-protective agent of the present invention, comprising an effective amount of a specific isoquinolinesulfonamide derivative can be effectively used for prophylaxis and treatment of not only myocardial diseases, such as myocardial infarction and complications of myocardial infarction (e.g., shock, arrhythmia and heart failure, which accompany myocardial infarction), but also myocardial cell injury which is caused by ischemia/reperfusion in the treatment of myocardial infarction, such as thrombolytic therapy, percutaneous transluminal coronary angioplasty or the like, or which is caused by an arterial blocking or a sudden change in hemodynamics during or after open heart surgery.

We claim:

1. A method for the prophylaxis and treatment of a myocardial disease which is caused by the influence of ischemia, or ischemia and reperfusion, and which results in the necrosis of myocardial cells, comprising administering to a patient suffering from or diagnosed to be susceptible to the myocardial disease an effective amount of an isoquinolinesulfonamide derivative represented by formula (I) or a pharmaceutically acceptable acid addition salt thereof:

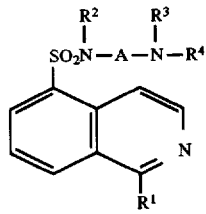

wherein $R^1$ represents a hydrogen atom, a chlorine atom or a hydroxyl group, and wherein:

when $R^1$ is a hydrogen atom, A represents a $C_2$–$C_6$ alkylene group, which is unsubstituted or substituted with at least one substituent selected from the group consisting of a $C_1$–$C_{10}$ alkyl group, a cinnamyl group, a phenyl group and a benzyl group; $R^2$ represents a hydrogen atom or a cycloalkyl group having 6 carbon atoms or less; $R^3$ represents a hydrogen atom, a straight or branched $C_1$–$C_6$ alkyl group, a cinnamyl group, a phenyl group or a benzyl group; or $R^2$ and $R^3$ together form an alkylene group having 4 carbon atoms or less, which is unsubstituted or substituted with at least one substituent selected from the group consisting of a $C_1$–$C_{10}$ alkyl group, a phenyl group and a benzoyl group; and $R^4$ represents a hydrogen atom, a straight or branched $C_1$–$C_6$ alkyl group, a phenyl group, a benzyl group, a benzoyl group, a cinnamyl group, a cinnamoyl group, a furoyl group, a group represented by the formula:

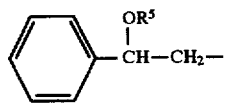

wherein $R^5$ represents a straight or branched $C_1$–$C_6$ alkyl group, or an amidino group represented by the formula:

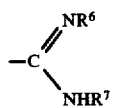

wherein each of $R^6$ and $R^7$ independently represents a hydrogen atom or a methyl group, or $R^6$ and $R^7$ together form a $C_2$–$C_4$ alkylene group; or $R^3$ and $R^4$ together with a neighboring nitrogen atom form a 5 or 6-membered heterocyclic group, which group optionally contains an oxygen atom; and when $R^1$ is a chlorine atom or a hydroxyl group, A represents a $C_2$–$C_6$ alkylene group, which is unsubstituted or substituted with at least one $C_1$–$C_6$ alkyl group; each of $R^2$ and $R^3$ independently represents a hydrogen atom, a straight or branched $C_1$–$C_6$ alkyl group or a cycloalkyl group having 6 carbon atoms or less, or $R^2$ and $R^3$ together form an ethylene or a trimethylene group, which is unsubstituted or substituted with at least one $C_1$–$C_6$ alkyl group; and $R^4$ represents a hydrogen atom, a $C_1$–$C_6$ alkyl group or an amidino group represented by the formula:

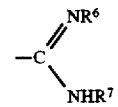

wherein each of $R^6$ and $R^7$ independently represents a hydrogen atom or a methyl group.

2. The method according to claim 1, wherein $R^1$ represents a hydrogen atom; A represents an ethylene group or a trimethylene group; $R^2$ and $R^3$ together form a trimethylene group when A represents an ethylene group, or form an ethylene group when A represents a trimethylene group; and $R^4$ represents a hydrogen atom.

3. The method according to claim 1, wherein $R^1$ represents a hydroxyl group; A represents an ethylene group or a trimethylene group; $R^2$ and $R^3$ together form a trimethylene group when A represents an ethylene group, or form an ethylene group when A represents a trimethylene group; and $R^4$ represents a hydrogen atom.

4. The method according to claim 1 or 2, wherein the isoquinolinesulfonamide derivative represented by formula (I) is 1-(5-isoquinolinesulfonyl)homopiperazine.

5. The method according to claim 1 or 3, wherein the isoquinolinesulfonamide derivative represented by formula (I) is 1-(1-hydroxy-5-isoquinolinesulfonyl)homopiperazine.

6. The method according to any one of claims 1 to 3, wherein the myocardial disease is myocardial infarction.

7. The method according to any one of claims 1 to 3, wherein the myocardial disease is a myocardial disease which is caused by the influence of ischemia and reperfusion and which results in the necrosis of myocardial cells.

8. A method for the prophylaxis and treatment of a myocardial disease which is caused by the influence of ischemia, or ischemia and reperfusion, and which results in the necrosis of myocardial cells, comprising administering to a patient suffering from or diagnosed to be susceptible to the myocardial disease an effective amount of an isoquinolinesulfonamide derivative represented by formula (I) or a pharmaceutically acceptable acid addition salt thereof:

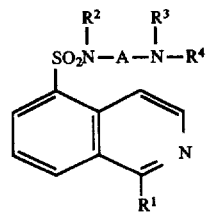

wherein $R^1$ represents a hydrogen atom, a chlorine atom or a hydroxyl group, and wherein:

when $R^1$ is a hydrogen atom, A represents a $C_2$–$C_6$ alkylene group, which is unsubstituted or substituted with at least one substituent selected from the group consisting of a $C_1$–$C_{10}$ alkyl group, a cinnamyl group, a phenyl group and a benzyl group; $R^2$ represents a hydrogen atom or a cycloalkyl group having 6 carbon atoms or less; $R^3$ represents a hydrogen atom, a straight or branched $C_1$–$C_6$ alkyl group, a cinnamyl group, a phenyl group or a benzyl group; or $R^2$ and $R^3$ together form an alkylene group having 4 carbon atoms or less, which is unsubstituted or substituted with at least one substituent selected from the group consisting of a $C_1$–$C_{10}$ alkyl group, a phenyl group and a benzoyl group; and $R^4$ represents a hydrogen atom, a straight or branched $C_1$–$C_6$ alkyl group, a phenyl group, a benzyl group, a benzoyl group, a cinnamyl group a cinnamoyl group, a furoyl group, and a group represented by the formula:

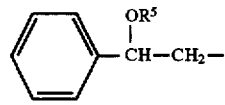

wherein $R^5$ represents a straight or branched $C_1$–$C_6$ alkyl group; or $R^3$ and $R^4$ together with a neighboring nitrogen atom form a 5 or 6-membered heterocyclic group, which group optionally contains an oxygen atom; and when $R^1$ is a chlorine atom or a hydroxyl group, A represents a $C_2$–$C_6$ alkylene group, which is unsubstituted or substituted with at least one $C_1$–$C_6$ alkyl group; each of $R^2$ and $R^3$ independently represents a hydrogen atom, a straight or branched $C_1$–$C_6$ alkyl group or a cycloalkyl group having 6 carbon atoms or less, or $R^2$ and $R^3$ together form an ethylene or a trimethylene group, which is unsubstituted or substituted with at least one $C_1$–$C_6$ alkyl group; and $R^4$ represents a hydrogen atom, a $C_1$–$C_6$ alkyl group or an amidino group represented by the formula:

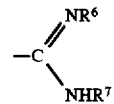

wherein each of $R^6$ and $R^7$ independently represents a hydrogen atom or a methyl group.

9. The method according to claim 8, wherein $R^1$ represents a hydrogen atom; A represents an ethylene group or a trimethylene group; $R^2$ and $R^3$ together form a trimethylene group when A represents an ethylene group, or form an ethylene group when A represents a trimethylene group; and $R^4$ represents a hydrogen atom.

10. The method according to claim 8, wherein $R^1$ represents a hydroxyl group; A represents an ethylene group or a trimethylene group; $R^2$ and $R^3$ together form a trimethylene group when A represents an ethylene group, or form an ethylene group when A represents a trimethylene group; and $R^4$ represents a hydrogen atom.

11. The method according to claim 8, wherein the myocardial disease is myocardial infarction.

12. The method according to claim 8, wherein the myocardial disease is a myocardial disease which is caused by the influence of ischemia and reperfusion and which results in the necrosis of myocardial cells.

* * * * *